United States Patent
Singh et al.

(10) Patent No.: US 9,441,252 B2
(45) Date of Patent: Sep. 13, 2016

(54) PROCESS FOR PRODUCING LIPIDS SUITABLE FOR BIOFUELS

(71) Applicant: INDIAN OIL CORPORATION LTD., Kolkata, West Bengal (IN)

(72) Inventors: Mahendra Pratap Singh, Faridabad (IN); Manoj Kumar, Faridabad (IN); Dheer Singh, Faridabad (IN); Deepak Kumar Tuli, Faridabad (IN); Ravinder Kumar Malhotra, Faridabad (IN)

(73) Assignee: INDIAN OIL CORPORATION LTD., Kolkata (IN)

( * ) Notice: Subject to any disclaimer, the term of this patent is extended or adjusted under 35 U.S.C. 154(b) by 0 days.

(21) Appl. No.: 14/347,885

(22) PCT Filed: Oct. 11, 2012

(86) PCT No.: PCT/IB2012/002016
§ 371 (c)(1),
(2) Date: Mar. 27, 2014

(87) PCT Pub. No.: WO2013/054170
PCT Pub. Date: Apr. 18, 2013

(65) Prior Publication Data
US 2014/0356917 A1 Dec. 4, 2014

(30) Foreign Application Priority Data

Oct. 12, 2011 (IN) .............................. 1315/KOL/2011

(51) Int. Cl.
| | | |
|---|---|---|
| C12P 7/64 | (2006.01) | |
| C12N 1/12 | (2006.01) | |
| C10L 1/02 | (2006.01) | |
| C11B 1/04 | (2006.01) | |
| C11B 1/10 | (2006.01) | |
| C11C 3/00 | (2006.01) | |
| C12R 1/89 | (2006.01) | |

(52) U.S. Cl.
CPC ................ *C12P 7/649* (2013.01); *C10L 1/02* (2013.01); *C10L 1/026* (2013.01); *C11B 1/04* (2013.01); *C11B 1/10* (2013.01); *C11C 3/003* (2013.01); *C12N 1/12* (2013.01); *C12P 7/64* (2013.01); *C10G 2300/1014* (2013.01); *C12R 1/89* (2013.01); *Y02E 50/13* (2013.01); *Y02P 30/20* (2015.11)

(58) Field of Classification Search
None
See application file for complete search history.

(56) References Cited

U.S. PATENT DOCUMENTS

2011/0104791 A1* 5/2011 Gajraj .................... A01G 33/00
435/257.1

FOREIGN PATENT DOCUMENTS

| WO | 04/001067 A2 | 12/2003 |
| WO | WO 2009/149027 | * 12/2009 |
| WO | WO 2010/042842 | * 4/2010 |

OTHER PUBLICATIONS

Xu et al., High quality biodiesel production from a microalga Chlorella prototheocoides by heterotrophic growth in fermenters., Journal of Biotechnology (2006), vol. 126, pp. 499-507.*
Weldy et al., Lipid Production by Dunaliella salina in Batch Culture: Effects of Nitrogen Limitation and Light Intensity. Journal of Undergraduate Research (2007), vol. VII, pp. 115-122.*
Definition of heterotrophic (last viewed on May 13, 2016).*
Kumar A et al., "Enhanced C02 fixation and biofuel production via microalgae: recent developments and future directions", Trends in Biotechnology, Elsevier Publications, Cambridge, GB, vol. 28, Issue 7, Jul. 1, 2010, pp. 371-380.
León-Bañares R. et al., "Transgenic microalgae as green cell-factories," Trends in Biotechnology, Elsevier Publications, Cambridge, GB, vol. 22, Issue 1, Jan. 1, 2004, pp. 45-52.
Maneeruttanarungroj C. et al., "A newly isolated green alga, *Tetraspora* sp. CU2551, from Thailand with efficient hydrogen production," International Journal of Hydrogen Energy, Elsevier Science Publishers B.V., Barking, GB, vol. 35, Issue 24, Dec. 2010, pp. 13193-13199.
Rupprecht et al., "From systems biology to fuel-Chlamydomonas reinhardtii as a model for a systems biology approach to improve biohydrogen production," Journal of Biotechnology, Elsevier Science Publishers, Amsterdam, NL, vol. 142, Issue 1, Jun. 1, 2009, pp. 10-20.

* cited by examiner

Primary Examiner — Alexander Kim
(74) Attorney, Agent, or Firm — Maschoff Brennan

(57) ABSTRACT

The present invention provides a cost effective biotechnological process for production of bio-fuels from isolated and characterized microalgae. The algal strains used in the present invention having higher biomass, higher lipid productivity, higher pH and temperature tolerance are selected from the group consisting of *Chlorella vulgaris* iOC-1, *Chlorella vulgaris* iOC-2, *Chlorella kessleri*, *Botrococcus bruni*, *Dunaliella salina* and *Nannochloris oculat* or a combination thereof having 95-100% similarity with 18s ribosomal nucleic acids nucleotide sequences (rDNA) given for Seq. ID I, Seq. ID 2, Seq. ID 3, Seq. ID 4, Seq. ID 5 and Seq. ID 6. The present process of bio-fuel production comprises the steps of producing lipid from green algae in bioreactors by various novel steps and extracting oil from dried algal cells and ultimately producing biodiesel by transesterification of the said extracted oil.

13 Claims, No Drawings

PROCESS FOR PRODUCING LIPIDS SUITABLE FOR BIOFUELS

FIELD OF THE INVENTION

The present invention is related to the field of biofuel. More particularly, the present invention is directed to a process for the production of lipids suitable for biofuel production from microalgae by heterotrophic cultivation.

BACKGROUND OF THE INVENTION

The need of energy is increasing continuously, because of increase in industrialization and population. The basic sources of this energy are petroleum, natural gas, coal, hydro and nuclear. The major disadvantage of using petroleum based fuels is atmospheric pollution created by the use of petroleum diesel. Petroleum diesel combustion is a major source of greenhouse gas (GHG). Apart from these emissions, petroleum diesel is also major source of other air contaminants including NOx, SOx, CO, particulate matter and Volatile Organic Compounds (VOC).

Biomass is one of the better sources of energy. Large-scale introduction of biomass energy could contribute to sustainable development on several fronts, environmentally, socially and economic. Bio-diesel (monoalkyl esters) is one of such alternative fuel, which is obtained by the transesterification of triglyceride oil with monohydric alcohols. Biodiesel fuel can be prepared from waste cooking oil, such as palm, soybean, canola, rice bran, sunflower, coconut, corn oil, fish oil, chicken fat and algae which would partly decrease the dependency on petroleum-based fuel.

Macroalgae has also been used in the production of biodiesel. Microalgae with higher oil content than plants are known and they are faster and easier to grow. Microalgae can provide several different types of renewable biofuels. These include methane produced by anaerobic digestion of the algal biomass, biodiesel derived from microalgal oil and photobiologically produced biohydrogen. The idea of using microalgae as a source of fuel is not new but it is now being taken seriously because of the extinguishing petroleum resources and, more significantly, the emerging concern about global warming that is associated with burning fossil fuels.

Microalgae comprise a vast group of unicellular photosynthetic, heterotrophic organisms which have an extraordinary potential for cultivation as energy crops. Microalgae are the great source of many highly valuable products such as polyunsaturated fatty acids, astaxanthin and bioactive compounds.

Microalgae can be grown in two different modes: Photoautotrophic and Heterotrophic mode of growth. Large-scale production of these products, however, has hindered by an ability to obtain high cell densities and productivities in photoautotrophic systems because of light penetration issues and uncontrolled growth conditions. High cell density processes suitable for heterotrophic cultures of microalgae may provide an alternative means for large-scale production of algal products of high value. The heterotrophic growth of algae holds many practical applications in industrial scale especially in a controlled manner to obtain highest biomass as well as lipid productivity.

In heterotrophic conditions algae can be grown on organic carbon sources, such as sugars and organic acids. This mode of culture eliminates the requirement for light and therefore, offers the possibility of greatly increased cell density and productivity. Some microalgae show rapid heterotrophic growth. Heterotrophic algal cultivation has been reported to provide not only a high algal biomass productivity, but high cellular oil content as well. Additionally the culture suffers from the contamination by undesired microbes. However, to date, the very few reports of such processes for microalgal cultivation have mostly been on lab-scale work/plant scale.

Xu et al 2006 (Han Xu, Xiaoling Miao and Qingyu Wu High quality biodiesel production from a microalga *Chlorella protothecoides* by heterotrophic growth in fermenters. Journal of Biotechnology Volume 126, Issue 4, 1 Dec. 2006, Pages 499-507) discussed high quality biodiesel production from a microalga *Chlorella protothecoids* through the technology of transesterification. The technique of metabolic controlling through heterotrophic growth of *C. protothecoides* was applied, and the heterotrophic *C. protothecoides* contained the crude lipid content of 55.2%. To increase the biomass and reduce the cost of alga, corn powder hydrolysate instead of glucose was used as organic carbon source in heterotrophic culture medium in fermenters. The result showed that cell density significantly increased under the heterotrophic condition, and the highest cell concentration reached 15.5 g L-1. Large amount of microalgal oil was efficiently extracted from the heterotrophic cells by using n-hexane, and then transmuted into biodiesel by acidic transesterification. The biodiesel was characterized by a high heating value of 41 MJ kg-1, a density of 0.864 kg L-1, and a viscosity of 5.2×10-4 Pa s (at 40° C.). The method has great potential in the industrial production of liquid fuel from microalga.

Li et al. 2007 reported (Li X F, Xu H, Wu Q Y (2007) Large-scale biodiesel production from microalga *Chlorella protothecoides* through heterotrophic cultivation in bioreactors. Biotechnol Bioeng 98:764-771) an integrated approach of biodiesel production from heterotrophic *Chlorella protothecoides* focused in bioreactors. Through substrate feeding and fermentation process controls, the cell density of *C. protothecoides* achieved 15.5 g $L^{-1}$ in 5 L, 12.8 g $L^{-1}$ in 750 L, and 14.2 g $L^{-1}$ in 11,000 L bioreactors, respectively. Resulted from heterotrophic metabolism, the lipid content reached 46.1%, 48.7%, and 44.3% of cell dry weight in samples from 5 L, 750 L, and 11,000 L bioreactors, respectively.

Liang et al (2009) reported (Liang Y, Sarkany N, Cui Y 2009 Biomass and lipid productivities of *Chlorella vulgaris* under autotrophic, heterotrophic and mixotrophic growth conditions. Biotechnology Letters July; 31(7):1043-9) biomass and lipid productivities of *Chlorella vulgaris* under different growth conditions. While autotrophic growth did provide higher cellular lipid content (38%), the lipid productivity was much lower compared with those from heterotrophic growth with acetate, glucose, or glycerol. Optimal cell growth (2 g l(−1)) and lipid productivity (54 mg l(−1) day(−1)) were attained using glucose at 1% (w/v) whereas higher concentrations were inhibitory. Growth of *C. vulgaris* on glycerol had a similar dose effects as those from glucose. Overall, *C. vulgaris* is mixotrophic.

US patent application 2009/0211150A1 discloses a method to produce biodiesel from algae using a strain of microalga *chlorella protothecoids*, by screening a specific strain with characteristics of high yield of biomass and high oil content, cultivating the screened strain for high-cell-density growth for up to 108 grams of dry cell weight per liter of the suspension in a bioreactor using solutions containing carbohydrates as feed, harvesting and drying the high density cultivated algal cells to extract oil from the dried algal cells, and producing the biodiesel by catalyzed transesterification using the extracted oil as feedstock.

In the prior art few microalgal strains have been cultured to produce lipids for biodiesel. However, lipids produced from these microalgal strains are mostly rich in unsaturated fatty acids which makes them unsuitable for biodiesel production. Therefore, there exists a need to have increased saturated fatty acids content in lipids from microalgal strain with higher biomass oil content using various cheap carbon sources for cultivation which ultimately makes the process more cost effective and applicable in terms of its industrial success.

OBJECT OF THE INVENTION

The principal object of the present invention is to provide a process to produce suitable lipids from heterotrophic cultivation of microalgae for biodiesel.

Another object is to provide a process where lipids are produced from microalgal strain with higher biomass and oil content.

Yet another object of the invention is to provide a process where lipids is produced from the microalgae which can withstand high temperature and high pH.

Still another object of the invention is to provide a process for production of biofuel where the microalgae is fed cheap source of carbohydrates like wheat flour, hydrolysate of lignocellulosic biomass, organic waste water streams like sewage treatment plant, water from distillery, fruit processing industry, dairy industry etc.

SUMMARY OF THE INVENTION

Accordingly, the present invention provides a novel and cost effective method to produce oil feedstock for the production of biofuel by heterotrophic growth of green microalgae in a bioreactor. The process of the present invention comprises the steps of isolation of high oil producing green algae with characteristics of high yield of biomass and high oil content; screening of the same for heterotrophic growth, inoculating the strain in a bioreactor for algal-seed-cells cultivation; transferring the cultivated algal-seed-cells into a second bioreactor for high-cell-density cultivation; feeding a second solution containing carbohydrates into the second bioreactor; harvesting the high density cultivated algal cells from the second bioreactor; drying the high density cultivated algal cells; extracting oil from dried algal cells; and producing the biodiesel by reaction of transesterification using the extracted oil as feedstock or using the biomass for gasification, fermentative biohydrogen, bioethanol, and biomethane production. The high-cell-density cultivation of the present invention further comprises heterotrophic cultivation of Chlorella vulgaris, C. kessleri, Botrococcus bruni, Dunaliella salina and Nannochloris oculata high oil content, preferably up to 58% dry cell weight. The carbohydrates solutions include but not limit to glucose or other monosaccharides, and/or disaccharides, or polysaccharides preferably with the concentration of glucose or other monosaccharides, disaccharides, polysaccharides, or hydrolysates of corn starch, wheat flour, hydrolysate of lignocellulosic biomass e.g. cheaper lignocellulosic biomass belonging to Lemna, baggase, sugar cane top, pine needle, wheat straw, rice straw etc, organic waste water streams like sewage treatment plant, water from distillery and fruit processing industry, dairy industry containing organic sugars, molasses preferably with concentration of the carbohydrates solutions being controlled between 0.01 and 100 gL$^{-1}$.

DETAILED DESCRIPTION OF THE INVENTION

The present invention comprises the steps of isolation of high oil producing green alga with characteristics of high yield of biomass and high oil content; screening of the same for heterotrophic growth, inoculating the strain in a bioreactor for algal-seed-cells cultivating; transferring the cultivated algal-seed-cells into a second bioreactor for high-cell-density cultivation; feeding a second solution containing carbohydrates into the second bioreactor; harvesting the high density cultivated algal cells from the second bioreactor; drying the high density cultivated algal cells; extracting oil from dried algal cells; and producing the biodiesel by reaction of transesterification using the extracted oil as feedstock or using the biomass for gasification, fermentative biohydrogen, bioethanol, and biomethane production.

The algal strains used for the process are Chlorella vulgaris iOC-1, Chlorella vulgaris iOC-2, Chlorella kessleri, Botrococcus bruni, Dunaliella salina and Nannochloris oculat or combination thereof. The said algae can be grown separately as well as in different combination providing better yield in terms of biomass and lipid content/composition. These algal strains have been well characterized by their 18s ribosomal nucleic acids. The partial genomic DNA sequences shows 95% to 100% sequence identities to the nucleic acid sequences selected from the group consisting of Seq. ID 1, Seq. ID 2, Seq. ID 3, Seq. ID 4, Seq. ID 5 and Seq. ID 6. and the algal strains shows higher temperature tolerance up to 52° C.

The source of carbohydrates fed in the bioreactor selected from the group consisting of pure sugar(s), hydrolysates of corn starch, wheat flour, hydrolysate of lignocellulosic biomass, organic waste water streams like sewage treatment plant, water from distillery and fruit processing industry, dairy industry containing organic sugars, molasses etc. The process of the present invention optionally comprises feeding of nitrogen into the bioreactor. The nitrogen is organic nitrogen which may be selected from the group consisting of glycine, yeast powder, yeast extract, peptone, ammonium chloride, urea, $KNO_3$, Ammonium nitrate, ammonia, or corn syrup.

feeding of phosphorus into the bioreactor. The phosphorus used in the bioreactor may be selected from the group consisting of di-ammonium phosphate, $K_2HPO_4$ or $KH_2PO_4$.

Isolation of Specific Algae

Soil and water samples were collected from different locations e.g. Effluent treatment plant (ETP), Yamuna River, Agra, agricultural soil. The water and soil sample were inoculated in 0.8% agar medium was prepared using media containing $KH_2PO_4$: 0.7 g/L, $K_2HPO_4$: 0.3 g/L, $MgSO_4.7H_2O$: 0.3 g/L, $FeSO_4.7H_2O$: 3 mg/L, Glycine: 0.1 g/L, vitamin $B_1$: 0.01 mg/L, A5 trace mineral solution 1.0 ml/L, wherein the A5 trace mineral solution comprises $H_3BO_3$, $Na_2MoO_4.2H_2O$, $ZnSO_4.7H_2O$, $MnCl_2.4H_2O$, and $CuSO_4.5H_2O$. A preferred A5 trace mineral solution comprises: $H_3BO_3$: 2.86 g/L, $Na_2MoO_4.2H_2O$: 0.039 g/L, $ZnSO_4.7H_2O$: 0.222 g/L, $MnCl_2.4H_2O$: 1.81 g/L, $CuSO_4.5H_2O$: 0.074 g/L. 1 g L-1 peptone, 2 g L-1 yeast extract, 4 g L-1 glucose, and antibiotics including ampicillin (sodium form), streptomycin sulfate, and kanamycin sulfate (100 mg L−1 each). After inoculation, the plates were wrapped and stored at 26° C. for 2-5 days. Single green colonies were picked and carefully transferred to a new plate. The purified colonies are selectively picked up and inoculated into flasks containing growth medium including but not limiting to components of basal medium under light conditions, for further culture.

Screening for Heterotrophic Growth

The micro-algal strains were inoculated into a 500-mL Erlenmeyer flasks containing 100-mL medium at 28° C. under continuous shaking at 180 rpm. Glucose with a concentration of 30 g/L and yeast extract with a concentration of 4 g/L are added into the basal medium. The heterotrophic media was incubated in the dark. The cell growth rates and cellular oil contents in different culture are then compared with each other to determine a specific strain with characteristics of the highest oil content and a high cell growth rate. The selected strain having ability to utilize sugar as carbon source and grow in heterotrophic conditions were selected for evaluation of their pH tolerance, temperature tolerance, ability to grow in wastewater, ability to grow in presence of different contaminants like hydrocarbon, heavy metals etc and strains having ability to grow in stringent condition with high cell density and higher lipid accumulation were selected for further study.

Identification and Characterization of Algal Strains

The selected algal strains were identified by their physiological, morphological characteristics. The 18S rRNA gene sequences as well as some specific morphological characteristics have been extensively studied by the present inventors. The resulting 18S rRNA gene sequences were aligned insilico and compared to the nucleotide sequences of some known microalge in GenBank database of the National Center for Biotechnology Information by using Basic Local Alignment Search Tool (BLAST®).

The partial genomic DNA sequences shows 95% to 100% sequence identities to the nucleic acid sequences selected from the group consisting of Seq. ID 1, Seq. ID 2, Seq. ID 3, Seq. ID 4, Seq. ID 5 and Seq. ID 6.

Algal-Seed-Cells Cultivation

The autotrophically grown cells of selected strain inoculated in the bioreactor aseptically containing culture medium for algal-seed-cells cultivation. The components of basal culture medium are: (mg/l) Glucose—9000, $KNO_3$—1011.1, $NaH_2PO_4 \cdot H_2O$—621, $Na_2HPO_4 \cdot 2H_2O$—89, $MgSO_4 \cdot 7H_2O$—246.5, EDTA—9.3, $H_3BO_3$—0.061, $CaCl_2 \cdot 2H_2O$—14.7, $FeSO_4 \cdot 7H_2O$—6.95, $ZnSO_4 \cdot 7H_2O$—0.287, $MnSO_4 \cdot H_2O$—0.169, $(NH_4)_6Mo_7O_{24} \cdot 4H_2O$—0.01235, $CuSO_4 \cdot 5H_2O$—0.00249, 1 g L−1 peptone, 2 g L−1 yeast extract, 4 g L−1 glucose, and antibiotics including ampicillin (sodium form), streptomycin sulfate, and kanamycin sulfate (100 mg L−1 each). The bioreactor was operated 28° C. in dark at 480 rpm. The pH maintained for pH range 6-7 and sampling was done every day to estimate the dry cell weight, chlorophyll content and lipid content regularly. Algal cell yield can be determined using various methods, including but not limiting to light intensity measurement of the cell suspension, such as OD540 nm of cell suspension. Preferable conditions such as glucose concentration, different nitrogen sources in the basal medium, temperatures, and shaking rate during algal-seed-cells cultivation in shaking flasks are determined by real-time light intensity measurement of the cell suspension. A preferable glucose concentration in a range of 2 to 40 g/L glucose is added in the basal medium. A preferable yeast extract in a range of 05 to 15 g/L yeast extract is added in the basal medium. A temperature in incubator is set between 10-50° C., preferably at 30° C. The shaking rate is controlled between 50 to 700 rpm, preferably at 300 rpm. The cells are harvested till the culture of algal seed cell enters into late-exponential-phase. The cell harvesting time before reaching the late exponential-phase is approximately at 120 hours.

High-Cell-Density Cultivation

The late-exponential-phase algal-seed-cells in the small bioreactor are transferred to a second bioreactor of 200 L containing 150 L media, for high-cell-density cultivation by process control and optimization. Glucose and yeast extract solutions are added into the basal culture medium initiate in the second bioreactor, preferably with 2 to 80 g/L glucose and 0.5 to 15 g/L yeast extract, further preferably with 45 g/L glucose and 6 g/L yeast extract. Parameters, such as the amount of inoculum, substrate (organic carbon and nitrogen) feeding, oxygen supply, stirring rate, temperature, pH, and time of cell harvest, and adjusted to optimize cell growths in the second bioreactor. Among the parameters, dissolved oxygen (DO) in the fermentation suspension for high-cell-density cultivation of heterotrophic algal cells in the bioreactor can be used to monitor the growth conditions, such as organic carbon sources in the reactor, biomass and accumulation of lips. On-line monitoring of the DO parameter is preferably used to monitor the growth conditions, and to adjust agitation speed and aerating rate. The carbohydrates solutions include but not limit to glucose or other monosaccharides, and/or disaccharides, or polysaccharides, preferably with the concentration of glucose or other monosaccharides, disaccharides, polysaccharides, or hydrolysates of corn starch, wheat flour, hydrolysate of lignocellulosic biomass, organic waste water streams like sewage treatment plant, water from distillery and fruit processing industry, dairy industry containing organic sugars, molasses preferably with concentration of the carbohydrates solutions being controlled between 0.01 and 100 gL.sup.−1.

The conditions for high-cell-density heterotrophic cultivation of the different strains were automatically monitored and set as follows:
  Inoculum amount of seed algal cells (V/V): 10-30%, preferably of 20%;
  Temperature at 15-52° C., preferably at 30±.0.5° C.;
    Aeration 100-200 L/h (1:1 vvm), preferably at 180 L/h;
  pH 6.0 to 9.0, preferably at 6.3.±.0.1;
  Concentration of glucose in medium: 20 g/L;
  DO over 20% controlled by increasing agitation and airflow, gradually increasing agitation speed from 100 to 600 rpm after a period of cultivation for about 88 hours, to maintain the dissolved oxygen at above 20% of saturation;
  When the cell density and/or the oil content reach desired values, preferably with the dry cell density reaching 24 g/L and the oil content reaching 58% of dry cell weight, the growth of the cells in the second reactor is terminated. The growth duration in said second bioreactor lasts about 120 hours.

The extreme conditions of pH and high temperature provide an advantage of inhibiting the growth of undesired microbes and obtaining less unsaturated fatty acids.

Harvesting the High Density Microalgal Cells from Bioreactor

After determining a sample of the high-cell-density heterotrophic cultivation to reach a desired dry biomass concentration, preferable between 12 to 24 g/L, dry biomass of the algal cell suspension from bioreactor is separated using a separation process, including but not limited to flocculation, filtration or centrifuge. The separated dry biomass may be in a form of powder or other solid forms.

Extracting the Oil from Dried Algal Cells

Lipids (oil) in heterotrophic cell powder are subsequently extracted by any well known solvent extraction methodology, e.g. the Soxhlet method, wherein N-hexane is used as the standard Soxhlet solvent for extracting oil from cells. Extraction is achieved by washing the cells repeatedly with pure solvent until no lipid is left in cells. Then the solvent in the extract is removed under reduced pressure. In an embodiment the selected microalgae was cultivated at temperature as high as 40-50° C. The lipid extracted from the algae on analysis for fatty acid composition were found to have more than 70% fatty acids saturated as compared to only 40% at 30° C. for the same algae. The selected algae have the ability to grow at extreme pH i.e., pH 5-9 and at temperature as high as upto 52 degree C.

Producing the Biodiesel from Microalgal Oil

These extracted microalgal oil can then be converted into biodiesel by known methods of transesterification, e.g. the enzymatic transesterification and/or acids and/or base catalyst.

EXAMPLE

Isolation and Selection of Heterotrophic Algal Strains

In the present invention, the soil and water samples were collected from Effluent Treatment Plant (ETP) of hydrocarbon processing industry. The collected water and soil samples were inoculated in 0.8% agar medium. The preparation was made using media containing $KH_2PO_4$: 0.7 g/L, $K_2HPO_4$: 0.3 g/L, $MgSO_4.7H_2O$: 0.3 g/L, $FeSO_4.7H_2O$: 3 mg/L, Glycine: 0.1 g/L, vitamin $B_1$: 0.01 mg/L, A5 trace mineral solution 1.0 ml/L, wherein the A5 trace mineral solution comprises $H_3BO_3$, $Na_2MoO_4.2H_2O$, $ZnSO_4.7H_2O$, $MnCl_2.4H_2O$, and $CuSO_4.5H_2O$. A preferred A5 trace mineral solution comprises: $H_3BO_3$: 2.86 g/L, $Na_2MoO_4.2H_2O$: 0.039 g/L, $ZnSO_4.7H_2O$: 0.222 g/L, $MnCl_2.4H_2O$: 1.81 g/L, $CuSO_4.5H_2O$: 0.074 g/L. 1 g L−1 peptone, 2 g L−1 yeast extract, 4 g L−1 glucose, and antibiotics including ampicillin (sodium form), streptomycin sulfate, and kanamycin sulfate (100 mg L−1 each). After inoculation, the plates were wrapped and stored at 26° C. for 2-5 days. Single green colonies were picked and carefully transferred to a new plate. The purified colonies are selectively picked up and inoculated into flasks containing growth medium, including but not limited to components of basal medium, for further culture.

The selected algal strains were characterized according to their 18S rRNA gene sequences, as well as some morphological characteristics. Six algae having six different sequences for 18S rRNA gene were obtained. These sequences were named as Seq ID1, Seq ID2, Seq ID3, Seq ID4, Seq ID5, Seq ID6. Seq. ID 1 represents DNA sequence of *Chlorella vulgaris* IOC-1 18S ribosomal RNA gene; Seq. ID 2 represents DNA sequence of *Chlorella vulgaris* IOC-2 18S ribosomal RNA gene; Seq. ID 3 represents DNA sequence of *Chlorella kessleri* 18S ribosomal RNA gene; Seq. ID 4 represents DNA sequence of *Botryococcus braunii* 18S ribosomal RNA gene; Seq. ID 5 represents *Dunaliella salina* 18S ribosomal RNA gene and Seq. ID 6 represents *Nannochloris oculata* 18S small subunit ribosomal RNA gene.

The resulting 18S rRNA gene sequences were aligned and compared to the nucleotide sequences of some known microalge in GenBank database of the National Center for Biotechnology Information by using Basic Local Alignment Search Tool (BLAST®). Five potential culture having ability to grow in heterotrophic conditions and accumulate high lipid content and higher biomass was identified as *Chlorella vulgaris*, *Chlorella kessleri*, *Botrococcus brunii*, *Dunaliella salina* and *Nannochloris oculata*.

Heterotrophic Growth in Bioreactor

The selected strain inoculated in the bioreactor aseptically containing culture medium for algal-seed-cells cultivation. The components of basal culture medium are: (Mg/l) Glucose—9000, $KNO_3$—1011.1, $NaH_2PO_4.H_2O$—621, $Na_2HPO_4.2H_2O$—89, $MgSO_4.7H_2O$—246.5, EDTA—9.3, $H_3BO_3$—0.061, $CaCl_2.2H_2O$—14.7, $FeSO_4.7H_2O$—6.95, $ZnSO_4.7H_2O$—0.287, $MnSO_4.H_2O$—0.169, $(NH_4)_6Mo_7O_{24}.4H_2O$—0.01235, $CuSO_4.5H_2O$—0.00249, 1 g L−1 peptone, 2 g L−1 yeast extract, 4 g L−1 glucose, and antibiotics including ampicillin (sodium form), streptomycin sulfate, and kanamycin sulfate (100 mg L−1 each). The bioreactor was operated 28° C. in dark at 480 rpm. The pH maintained for pH range 6-7 and sampling was done every day to estimate the dry cell weight, chlorophyll content and lipid content regularly. Algal cell yield can be determined using various methods, including but not limiting to light intensity measurement of the cell suspension, such as OD540 nm of cell suspension. Preferable conditions such as glucose concentration, different nitrogen sources in the basal medium, temperatures, and shaking rate during algal-seed-cells cultivation in shaking flasks are determined by real-time light intensity measurement of the cell suspension. A preferable glucose concentration in a range of 2 to 40 g/L glucose is added in the basal medium. A preferable yeast extract in a range of 05 to 15 g/L yeast extract is added in the basal medium. A temperature in incubator is set between 10-50° C., preferably at 30° C. The shaking rate is controlled between 50 to 700 rpm, preferably at 300 rpm. The cells are harvested till the culture of algal seed cell enters into late-exponential-phase. The cell harvesting time before reaching the late exponential-phase is approximately at 168 hours.

The late-exponential-phase algal-seed-cells in the small bioreactor are transferred to a second bioreactor of 200 L containing 150 L media, for high-cell-density cultivation by process control and optimization. Glucose and yeast extract solutions are added into the basal culture medium initiate in the second bioreactor, preferably with 2 to 80 g/L glucose and 0.5 to 15 g/L yeast extract, further preferably with 45 g/L glucose and 6 g/L yeast extract. Parameters, such as the amount of inoculum, substrate (organic carbon and nitrogen) feeding, oxygen supply, stirring rate, temperature, pH, and time of cell harvest, and adjusted to optimize cell growths in the second bioreactor. Among the parameters, dissolved oxygen (DO) in the fermentation suspension for high-cell-density cultivation of heterotrophic algal cells in the bioreactor can be used to monitor the growth conditions, such as organic carbon sources in the reactor, biomass and accumulation of lips. On-line monitoring of the DO parameter is preferably used to monitor the growth conditions, and to adjust agitation speed and aerating rate. The carbohydrates solutions include but not limit to glucose or other monosaccharides, and/or disaccharides, or polysaccharides, preferably with the concentration of glucose or other monosaccharides, disaccharides, polysaccharides, or hydrolysates of corn starch, wheat flour, hydrolysate of lignocellulosic biomass, organic waste water streams like sewage treatment plant, water from distillery and fruit processing industry, dairy industry containing organic sugars, molasses preferably with concentration of the carbohydrates solutions being controlled between 0.01 and 100 gL.sup.−1.

The conditions for high-cell-density heterotrophic cultivation of the different strains were automatically monitored and set as follows:

Inoculum amount of seed algal cells (V/V): 20%;
Temperature at 30.+−.0.5.° C.
Aeration 180 L/h;
pH 7.3.±.0.1;
Concentration of glucose in medium: 20% (w/v)

DO over 20% controlled by increasing agitation and airflow, gradually increasing agitation speed from 100 to 600 rpm after a period of cultivation for about 88 hours, to maintain the dissolved oxygen at above 20% of saturation;

When the cell density and/or the oil content reach desired values, preferably with the dry cell density reaching 24 g/L and the oil content reaching 41% of dry cell weight, the growth of the cells in the second reactor is terminated. The growth duration in said second bioreactor lasts about 120 hours. Cell growth is measured by the absorbance of the suspension at 540 nm and dry cell weight. 1.5 ml of algal culture was taken in pre-weighed Eppendorf tubes, centrifuged at 8000 rpm for 5 minutes. The supernatant media was removal using micropipette and the algae pellet at the bottom was dried at 105° C. until the constant weight was achieved. The dry weight of algae biomass was determined gravimetrically and growth was expressed in terms of dry weight. Lipid measurements were made by using a mixture of methanol, chloroform, and water. A culture sample is collected at three points during the experiments for lipid analysis. The culture sample is centrifuged at 3,500 rpm for 10 minutes in a large (200 ml) plastic centrifuge tube; the pelleted cells along with 35 ml of supernatant are then transferred to a plastic centrifuge tube (45 ml) to be re-centrifuged again at 5000 rpm for 10 minutes. The supernatant is removed by pipette. The pellet is then resuspended with 4 ml of DI $H_2O$, then 10 ml of methanol and 5 ml of chloroform is added, resulting in a 10:5:4 ratio of methanol:chloroform:water. At this ratio, all solvents are miscible and form one layer. After overnight extraction on a shaker table, 5 ml of water and 5 ml of chloroform are added which results in a 10:10:9 ratio of methanol:chloroform:water. Tubes are centrifuged for 10 minutes at 5000 rpm. At this solvent ratio, two layers are formed, a water methanol upper layer and chloroform lower layer. The chloroform lower layer which contains the extracted lipids is then removed by Pasteur pipette and placed into a pre-weighed vial. After the first extraction, 10 ml of additional chloroform is added to conduct a second extraction. The additional 10 ml of chloroform again results is a 10:10:9 methanol:chloroform:water ratio and two layers are formed. The tube is centrifuged at 3,500 rpm for 10 minutes, and the lower chloroform layer is removed by Pasteur pipette and placed into another pre-weighed vial. The chloroform is evaporated by heating in a 55° C. water bath under a constant stream of nitrogen gas. After 1 hour in a 105° C. oven, vials are weighed again. The weight difference represents weight of lipids extracted from the culture sample. The extracted lipid was analysed by gas chromatography as per method described in prior art. The lipid showed fatty acid suitable for biodiesel production.

TABLE I

The Bio-mass and oil content of micro-algal species obtained under heterotrophic conditions

| Strain | Biomass (g (DCW)/l) | Oil Content (% w/w (DCW)) |
|---|---|---|
| Chlorella vulgaris IOC-1 | 16.82 | 29.8 |
| C. vulgaris IOC-2 | 12.01 | 27.4 |
| C. kessleri | 11.08 | 29.4 |
| Botrococcus bruni, | 12.8 | 41.5 |
| Dunaliella salina | 24.5 | 32.5 |
| Nannochloris oculata | 15.4 | 29.7 |

SEQ ID 1 to 6:
>Chlorella vulgaris for 18S ribosomal RNA strain: IOC-1

SEQ 1

```
TTTCATTCAAATTTCTGCCCTATCAACTTTTGATGGTAGGATAGAGGCCTACCATGGTGGTAAC
GGGTGACGGAGGATTAGGGTTCGATTCCGGAGAGGGAGCCTGAGAAACGGCTACCACATCCAAG
GAAGGCAGCAGGCGCGCAAATTACCCAATCCTGACACAGGGAGGTAGTGACAATAAATAACAAT
ACTGGGCCCGATCAGGTCTGGTAATTGGAATGAGTACAATCTAAACCCCTTAACGAGGATCAAT
TGGAGGGCAAGTCTGGTGCCAGCAGCCGCGGTAATTCCAGCTCCAATAGCGTATATTTAAGTTG
CTGCAGTTAAAAAGCTCGTAGTTGGATTTCGGGTGGGACCTGCCGGTCCGCCGTTTCGGTGTGC
ACTGGCAGGGCTCACCTTGTTGCCGGGGACGGGCTCCTGGGCTTCACTGACCGGGACTCGGAGT
CGGCGCTGTTACTTTGAGTAAATTAGAGTGTTCAAAGCAGGCCTACGCTCTGAATACATTAGCA
TGGAATAACACGATAGGACTCTGGCCTATCCTGTTGGTCTGTAGGACCGGAGTAATGATTAAGA
GGGACAGTCGGGGGCATTCGTATTTCATTGTCAGAGGTGAAATTCTTGGATTTATGAAAGACGA
ACTACTGCGAAAGCATTTGCCAAGGATGTTTTCATTAATCAAGTCCGCGAGTTGGGGGCTCGAA
GACGATTAGATACCGTCCTAGTCTCAACCATAAACGATGCCGACTAGGGATCGGCGGATGTTTC
TTCGATGACTCCGCCGGCACCTTATGAGAAATCAAAGTTTTTGGGTTCCGGGGGGAGTATGGTC
GCAAGGCTGAAACTTAAAGGAATTGACGGAAGGGCACCACCAGGCGTGGAGATTCTGGCTTAAT
TTGACTCAACACGGGAAAACTTACCAGGTCCAGACATAGTGAGGACTGACAGATTGAGACTCTT
TCTTGATTCTATGGGTGGTGGTGCATGGCCGTTCTTAGTTGGTGGGTTGCCTTGTCAGGTTGAT
TCCGGTAACGAACGAGACCTCAGCCTGCTAAATAGTCACGGTTGGTTCGCCAGCCGGCGGACTT
```

```
CTTAGAGGGACTATTGGCGACTAGCCAATGGAAGCATGAGGCTATAACAGGTCTGTGATGCCCT
TAGATGTTCTGGGCCGCACGCGCGCTACACTGATGCATTCAACGAGATTAGCCTTGGCCGAGAG
GCCCGGGTAATCTTCGAAACTGCATCGTGATG
```

>Chlorella vulgaris for 18S ribosomal RNA strain: IOC-2

SEQ 2
```
AAAAGGCCGACCGGGCTTCTGCCCGACTCGCGGTGAATCATGATAACTTCACGAATCGCATGGC
CTTGTGCCGGCGATGTTTCTTTCAAATTTCTGCCCTATCAACTTTTGATGGTAGGATAGAGGCC
TACCATGGTGGTAACGGGTGACGGAGGATTAGGGTTCGATTCCGGAGAGGGACCTGAGAAACG
GCTACCACATCCAAGGAAGGCAGCAGGCACGCAAATTACCCAATCCTGACACAGGGAGGTAGTG
ACAATAAATAACAATACTGGGCCTTGTCAGGTCTGGTAATTGGAATGAGTACAATCTAAACCCC
TTAACGAGGATCAATTGGAGGGCAAGTCTGGTGCCAGCAGCCGCGGTAATTCCAGCTCCAATAG
CGTATATTTAAGTTGCTGCAGTTAAAAAGCTCGTAGTTGGATTTCGGGTGGGACCTGCCGGTCC
GCCGTTTCGGTGTGCACTGGCAGGGCTCACCTTGTTGCCGGGGACGGGCTCCTGGGCTTCACTG
TCCGGGACTCGGAGTCGGCGCTGTTACTTTGAGTAAATTAGAGTGTTCAAAGCAGGCCTACGCT
CTGAATACATTAGCATCGAATAACACGATAGGACTCTGGCATATCCTGTTGGTCTGTAGGACCG
GAGTAATGATTAAGAGGGACAGTCTGGGGCATTCGTATTTCATTGTCAGAGGTGAAATTCTTGG
ATTTATGAAAGACGAACTACTGCCCTAGCATTTGCCAAGGATGTTTTCATTAATCAAGAACGAA
AGTTGGGGGCTCGAAGACGATTAGATACCGTCCTAGTCTCAAGCATAAACGATGCCGACTAGGG
ATCGGCGGATGTTTCTTCGATGACTCCGCCGGCACCTTATGAGATATCAAAGTTTTTAGCTTCC
GGGGGGAGTATGGTCGCAAGGCTGAAACTTAAAGGAATTGACGGAAGGGCACCACCAGGCGTGG
AGCCTGCGGCTTAAGGAGACTCAACACGGGAAAACTTACGAGGTCCAGACATAGTGAGGATTGA
CAGATTGAGAGCTCTTTCTTGATTCTATGGGTGGTGGTGCATGGCCGTTCTTAGTTGGTGGGTT
GCCTTGTCAGGTTGATTCCGGTAACGAACGAGACCTCAGCCTGCTAAATAGTCACGGTTGGTTC
GCCAGCCGGCGGACTTCTTAGAGGGAAATGCCTAGTAAGCGC
```

>Chlorella kessleri 18S ribosomal RNA

SEQ 3
```
CGTAAATCCCGACTTCTGGAAGGGACGTATTTATTAGATTTAAGGCCGACCCGGCTCTGCCGGT
CTCGCGGTGAATCATGATAACTTCACGAATCGCATGGCTTGCGCCGGCGATGTTTCATTCTTT
TTTCTGCCCTATCAACTTTCGATGGTAGGATAGAGGCCTACCATGGTGGTAACGGGTGACGGAG
GATTAGGGTTCGATTCCGGAGAGGGAGCCTGAGAAACGGCTACCACATCCAAGGAAGCCAGCAG
GCGCGCAAATTACCCAATCCTGACACAGGGAGGTAGTGACAATAAATTTCAATACCGGGCCTTT
TCAGGTCTGGTAATTGGAATGAGTACAATCTAAACCCCTTAACGAGGATCAATTGGAGGGCAAG
TCTGGTGCCAGCAGCCGCGGTAATTCCAGCTCCAATAGCGTATATTTAAGTTGCTGCAGTTAAA
AAGCTCGTAGTTGGATTTCGGGCGGGGCCTGCCGGTCCGCCGTTTGGGTGTGCACAGGCAGGGC
CCGCCTTGTTGCCGGGGACGGGCTCCTGGGCTTCACTGTCCGGGACTCGGAGTTGGCGCTGTTA
CTTTGAGTAAATTAGAGTGTTCAAAGCAGGCCTACGCTCTGAATGCATTAGCATGGAATAACAC
GATAGGACTCTGGCCTATCCTGTTGGTCTGTAGGACCGGAGTAATGATTAAGAGGGACAGTCGG
GGGCATTCGTATTTCGATGTCAGAGGTGAAATTCTTGGATTTTCGAAAGACGAACTACTGCGAA
AGCATTTGCCAAGGATGTTTTCATTAATCAAGAACGAAAGATGGGGGCTCGAAGACGATTAGAT
ACCGTCCTAGTCTCAACCATAAACGATGCCGACTAGCGATCGGCGGATGTTTCTTCGATGACTC
CGCCGGCACCTTATGAGAAATCAAAGTTTTTGGGTTCCGGGGGAGTATGGTCGCAAGGCTGAAG
ACTTGGGGGAATTGACGGAAGGGCACCACCATGCGTGGAGCCTGCGGCTTAATTTGACTCAACA
CGGGAAAACTTACCAGGTCCAGACATAGTGCGGATTGACAGATTGAGAGCTCTTTCTTGATTCT
ATGGGTGGTGGTGCATGGCCGTTCTTAGTTGGTGGGTTGCCTTGTCAGGTTGATTCCGGTAACG
AACGAGACCTCAGCCTGCTAAATCGTCACGGCCTCCTCGGGGGCCGGCAGACTTCTTAGAGGGA
CTATTGGCGACTAGCCAATGGAATCATGAGGCAATAACAGGTCTGTGATGCCCTTAGATGCCCT
GGGCCGCACGCGCGCTACTCTGATGCAATCAACGAGCCTAGCCTTGG
```

> Botryococcus braunii 18S ribosomal RNA gene

SEQ 4
```
TATTTATTAGATAAAAGGCTGACCGGGCTCGCCCGACTCTTGCTGACTCATGATAACTCGACGG
ATCGCACGGGCTTGTCCCGGCGACGTTTCATTCGCTTTTCTGCCCTATCAACTGTCGATGGTAC
GGTAGTGGCCTACCATGGTGTTCACGGGTGACGGAGAATTAGGGTTCGATTCCGGAGAGGGCGC
CTGAGAGACGGCGACCACATCCAAGGCCGGCAGCAGGCGCGCAAATTACCCAATCCTGACACAG
GGAGGTAGTGACAATAAATAACAATATCGGGGTTTCCAAACTCTGATAATTGGAATGAGTACAA
TCTAAAATCCTTAACGAGGATCAATTGGAGGGCAAGTCTGGTGCCAGCAGCCGCGGTAATTCCA
GCTCCAATAGCGTATACCCAAGTTGTTGCAGTTAAGCTGCTGTAGTCGGACTTCGGGTTCGGGG
CCGGCGGTCCGCCGACTGGTGTGCCATGCCGGGCCCCGCCTTGCTGCCGGAGATGGGATCCTGG
GCTTCGCTGTCCGGACCCGGACTCGGCGTGGTTACTTTGAGTAAATTAGAGTGTTCAAAGCAG
GCCTACGCTCTGAATATGTTAGCATGGAATAACGCGATAGGACTCTGGCCTATCTTGTTGGTCT
GTGGGACCGGAGTAATGATTAAGAGGGACAGTCGGGGGCATTCGTATTTCATTGTCAGGGGTCA
AATTCTTGGATTTATGAAAGACGGACTACTGCGAAAGCATTTGCCAAGGATGTTTTCATTGATC
AAGAACGAAAGTTGGGGGCTCGAAGACGATTAGATACCGTCCTAGTCTCAACCATAAACGATGC
CGACTAGGGATTGGTGGTGTTCTTTTGACGACCCCTCCAGCACCTTATGAGAAATCAAAGTTT
TTGGGTTCCGGGGCGAGTATGGTCGTAAGGCTGGAACTTAAAGGAATTGACGGAAGGGCACCAC
CAGGCGTGGAGCCTGCGGCTTAATTTGACTCAACACGGGAAAACTTACCAGGTCCAGACATAGT
GAGGATTGACAGATTGAGAGCTCTTCCTTGATTCTATGGGTGGTGGTGCATGGCCGTTCTTAGT
TGGTGGGTTGCCTTGTCAGGTTGATTCCGGTAACGAACGAGACCTCAGCCTGCTAAATAGTCCG
ACCAGGTTCGCCCAGGCCGCCGACTTCTTAGAGGGACTCTCGGCGACTAGCCGGAGGAAGTGTG
AGGCGATAACAGGACTGTG
```

SEQ 5
> Dunaliella salina 18S ribosomal RNA gene
```
ATTAGATGGTACCTTTACTCGGATAACCGTAGTAATTCTAGAGCTAATACGTGCGTAAATCCCG
ACTTCTGGAAGGGACGTATTTATTAGATAAAAGGCCAGCCGGGCTTGCCCGACTCTTGGCGAAT
CATGATAACTTAACGAATCGCACGGCTTTATGCCGGCGATGTTTCATTCAAATTTCTGCCCTAT
CAACTTTCGATGGTAGGATAGAGGCCTACCATGGTGGTAACGGGTGACGGAGGATTAGGGTTCG
ACCCCGGAGAGGGAGCCTGAGATTCGGCTACCAAATCCCAGGAAGGCAGCAGGCGCGCAAATTA
CCCAATCCCAACACGGGGATGTAGTGACAATAAATAACAATACCGGGCATTTTTGTCTGGTAAT
```

-continued

```
TGGAATGAGTACAATCTAAATCCCTTAACGAGTATCCATTGGAGGGCAAGTCTGGTGAAAGCAG
CCGCGGTAATTCCAGCTCCAATAGCGTATATGTAAGTTGTTGCAGTTAAAAAGCTCGTAGTTGG
ATTTCGGGTGGGTTGTAGCGGTCAGCCTTTGGTTAGTACTGCTACGGCCTACCTTTCTGCCGGG
GACGAGCTCCTGGGCTTAACTGTCCGGGACTCGGAATCGGCGAGGTTACTCTGAGTAAATTAGA
GTGTTCAAAGCAAGCCTACGCTCTGAATACATTAGCATGGAATAACACGATCGGACTCTGGCTT
ATCTTGTTGGTCTGTAAGACCGGAGTAATGATTAAGAGGGACAGTCGGGGCCATTCGTATTTCA
CTGTCAGAGGTGAAATTCTTGGATTTTGAAAGACGAACTTCCTGCGAAAGCATTTGCCAAGGAT
GTTTTCATTAATCCAAGAACGAAAGTTGGGGGCTCGAAGACGATTAGATACCAGTCGTAGTCTC
AACCATAAACGATGCCGACTTAGGGATTGGCAGGTGTTTCGTTGATGACCCTGCCAGCACCTTT
ATGAGAAATCACAGTTTTTTGGGTTCCGGGGGGAGTATGGTCGCAAGGCTGAAACTTAAAGGAA
TTGACGGAAGGGCACCACCAGGCGTGGAGCATGCGGCTTAATTAGACTCAACACGGGAAAACTT
ACCAGGTCCAGACACGGGGAGGATTGACAGATTGAGAGCTCTTTCTTGATTCTGTGGGTGGTGG
TGCATGGCCGTTCTTAGTTGGTGGGTTGCCTTGTCAGGTTGATTCCGG
                                                           SEQ 6
> Nannochloris oculata 18S small subunit ribosomal RNA gene
TATAAACTGCTTTATACTATGAAACTGCGAATGGCTCATTAAATCAGTTATAGTTTATTTGATG
GTACCTACTTACTCGGATAACCGTAGTAATTCTAGACGTAATACGTGCGCACATCCCGACTTCT
GGAAGGGACGTATTTATTAGATAAAAGGCCGACCGGATTTTTCCGACTCGCGGTGACTCATGAT
AACTTCACGAATCGCATGGCCTCGTGCCGGCGATGTTTCATTCAAATTTCTGCCCTATCGGCTT
TTGATGGTAGGATAGAGGCCTACCATGGTGGTAACGGGTGACGGAGAATTAGGGTTCGATTCCG
GAGAGGGAGCCTGAGAAACGGCTACCCACATCCAAGGAAGGCGCAGGCGCGCAAATTACCCAAT
CCTGACACAGGGAGGTAGTGACAATAAATAACAATACCGGGCCTTTGGTCTGGTAATTGGAATG
AGTACAACCTAAACACCTTAACGAGGATCAATTGGAGGGCAAGTCTGGTGCCAGCAGCCGCGGT
AATTCCAGCTCCAATAGCGTATATTTAAGTTGCTGCAGTTAAAAAGCTCGTAGTTGGATTACGG
GTGGGGCCTGCCGGTCCGCCGTTTCGGTGTGCACTGGCCGGGCCCACCTTGTTGCCGGGGACGG
GCTCCTGGGCTTCGCTGTCCGGGACCCGGAGTCGGCGAGGTTACTTTGAGTAAAATAGAGTGTT
CAAAGCAGGCCTACGCTCTGAATAATTAGCATGGAATAACACGATAGGACTCAGGCCTATCCTG
TTGGTCTGTAGGACCGGAGTAATGATTAAGAGGGACAGTCGGGGCATTCGTATTTCATTGTCA
GAGGTGAAATTCTTGGATTTATGAAAGACGAACTACTGCGAAAGCATTTGCCAAGGATGTTTTC
ATTAATCAAGAACGAAAGTTGGGGCTCGAAGACGATTAGATACCGTCCTAGTCTCAACCATAA
ACGATGCCGACTAGGGATCGGCGGGTGTTTTTTGATGACCCCGCCCCCACCTTATGAGAAATC
AAAGTTTTTGGGTTCCGGGGGGAGTATGGTCGCAAGGCTGAAACTTAAAGGAATTGACGGAAGG
GCACCACCAGGCGTGGAGCCTGCGGCTTAATTTGACTCAACACGGGAAAACTTACCAGGTCCAG
ACATAGTGAGGATTGACAGATTGAGAGCTCTTTCTTGATTCTATGGGTGGTGGTGCATGGCCGT
TCTTAGTTGGTGGGTTGCCTTGTCAGGTTGATTCCGGTGACGAACGAGACCTCAGCCTGCTAAC
TAGTCACGCGTGCTCCGGCACGCGGCGGACTTCTTAGAGGGACTATTGGCGACTAGCCAATGGA
TGCATGAGGCAATAACAGGTCTGTGATGCCCTTAGATGTTCTGGGCCGCACGCGCGCTACACTG
ATGCATTCAACGAGCCTATCCTTGGCCGAGAGG
```

We claim:

1. A process for producing bio-fuels consisting:
   (a) selecting a microalgae comprising a polynucleotide having 100% identity with 18s ribosomal nucleic acids nucleotide sequences (rDNA) of SEQ ID NO: 5,
   (b) culturing the said microalgae heterotrophically in a culture medium at pH of 9 and temperature of 52° C.,
   (c) harvesting the microalgal cells of step (b); and
   (d) extracting oil from the harvested algal cells obtained in step (c) having 70% saturated fatty acids to produce biodiesel.

2. The process as claimed in claim 1, wherein said cell-density is between 11 to 24 g/L (dry cell weight basis) and 100-200 g/l (wet weight basis).

3. The process as claimed in claim 1, wherein the oil content ranges from 22-58% dry cell weight.

4. The process as claimed in claim 1, wherein the culture medium comprises of at least one carbon source, one nitrogen source and one phosphorus source.

5. The process as claimed in claim 4, wherein the carbon source is selected from a group consisting of pentoses, hexoses sugar, monosaccharide, disaccharides and polysaccharides.

6. The process as claimed in claim 4, wherein the concentration of said at least one of hexoses or pentoses or other monosaccharides, disaccharides, and polysaccharides, in bioreactor is controlled between 0.01 and 100 g/L.

7. The process as claimed in claim 4, wherein the source of carbon is selected from the group consisting of pure sugar(s), hydrolysates of corn starch, wheat flour, hydrolysate of lignocellulosic biomass along with, organic waste water streams like sewage treatment plant, wastewater from crude oil refining industry containing hydrocarbons, water from distillery, fruit processing industry dairy industry, molasses, and organic material.

8. The process as claimed in claim 4, wherein the nitrogen is selected from the group consisting of glycine, yeast powder, yeast extract, peptone, ammonium chloride, urea, KNO3, ammonium nitrate, ammonia, corn syrup and nitrogen containing compounds present in said wastewater stream.

9. The process as claimed in claim 1, wherein initial inoculum for heterotrophic growth is prepared under phototrophic conditions and then inoculated in a bioreactor maintained under heterotrophic condition.

10. The process as claimed in claim 9, wherein amount of inoculum in the bioreactor is between 0.01% and 50% by volume.

11. The process as claimed in claim 1, wherein the medium in reactor is agitated with a speed of between 5 to 1,000 rpm.

12. The process as claimed in claim 9, wherein amount of inoculum in the bioreactor is 20% by volume.

13. The process as claimed in claim 1, wherein the medium in reactor is agitated with a speed of 700 rpm.

* * * * *

SEQUENCE LISTING

<160> NUMBER OF SEQ ID NOS: 6

<210> SEQ ID NO 1
<211> LENGTH: 1249
<212> TYPE: DNA
<213> ORGANISM: Chlorella vulgaris

<400> SEQUENCE: 1

```
tttcattcaa atttctgccc tatcaacttt tgatggtagg atagaggcct accatggtgg      60
taacgggtga cggaggatta gggttcgatt ccggagaggg agcctgagaa acggctacca     120
catccaagga aggcagcagg cgcgcaaatt acccaatcct gacacaggga ggtagtgaca     180
ataaataaca atactgggcc cgatcaggtc tggtaattgg aatgagtaca atctaaaccc     240
cttaacgagg atcaattgga gggcaagtct ggtgccagca gccgcggtaa ttccagctcc     300
aatagcgtat atttaagttg ctgcagttaa aaagctcgta gttggatttc gggtgggacc     360
tgccggtccg ccgtttcggt gtgcactggc agggctcacc ttgttgccgg gacgggctc     420 ctgggcttca ctgaccggga ctcggagtcg gcgctgttac tttgagtaaa ttagagtgtt     480
caaagcaggc ctacgctctg aatacattag catggaataa cacgatagga ctctggccta     540
tcctgttggt ctgtaggacc ggagtaatga ttaagaggga cagtcggggg cattcgtatt     600
tcattgtcag aggtgaaatt cttggatttta tgaaagacga actactgcga aagcatttgc     660
caaggatgtt ttcattaatc aagtccgcga gttgggggct cgaagacgat tagataccgt     720
cctagtctca accataaacg atgccgacta gggatcggcg gatgtttctt cgatgactcc     780
```

| | | |
|---|---|---|
| gccggcacct tatgagaaat caaagttttt gggttccggg gggagtatgg tcgcaaggct | 840 | |
| gaaacttaaa ggaattgacg gaagggcacc accaggcgtg gagattctgg cttaatttga | 900 | |
| ctcaacacgg gaaaacttac caggtccaga catagtgagg actgacagat tgagagctct | 960 | |
| ttcttgattc tatgggtggt ggtgcatggc cgttcttagt tggtgggttg ccttgtcagg | 1020 | |
| ttgattccgg taacgaacga gacctcagcc tgctaaatag tcacggttgg ttcgccagcc | 1080 | |
| ggcggacttc ttagagggac tattggcgac tagccaatgg aagcatgagg ctataacagg | 1140 | |
| tctgtgatgc ccttagatgt tctgggccgc acgcgcgcta cactgatgca ttcaacgaga | 1200 | |
| ttagccttgg ccgagaggcc cgggtaatct tcgaaactgc atcgtgatg | 1249 | |

<210> SEQ ID NO 2
<211> LENGTH: 1194
<212> TYPE: DNA
<213> ORGANISM: Chlorella vulgaris

<400> SEQUENCE: 2

| | | |
|---|---|---|
| aaaaggccga ccgggcttct gcccgactcg cggtgaatca tgataacttc acgaatcgca | 60 | |
| tggccttgtg ccggcgatgt ttctttcaaa tttctgccct atcaactttt gatggtagga | 120 | |
| tagaggccta ccatggtggt aacgggtgac ggaggattag ggttcgattc cggagaggga | 180 | |
| gcctgagaaa cggctaccac atccaaggaa ggcagcaggc acgcaaatta cccaatcctg | 240 | |
| acacagggag gtagtgacaa taaataacaa tactgggcct tgtcaggtct ggtaattgga | 300 | |
| atgagtacaa tctaaacccc ttaacgagga tcaattggag ggcaagtctg gtgccagcag | 360 | |
| ccgcggtaat tccagctcca atagcgtata tttaagttgc tgcagttaaa agctcgtag | 420 | |
| ttggatttcg ggtgggacct gccggtccgc cgtttcggtg tgcactggca gggctcacct | 480 | |
| tgttgccggg gacgggctcc tgggcttcac tgtccgggac tcggagtcgg cgctgttact | 540 | |
| ttgagtaaat tagagtgttc aaagcaggcc tacgctctga atacattagc atcgaataac | 600 | |
| acgataggac tctggcatat cctgttggtc tgtaggaccg gagtaatgat taagagggac | 660 | |
| agtctggggc attcgtattt cattgtcaga ggtgaaattc ttggatttat gaaagacgaa | 720 | |
| ctactgccct agcatttgcc aaggatgttt tcattaatca agaacgaaag ttgggggctc | 780 | |
| gaagacgatt agataccgtc ctagtctcaa gcataaacga tgccgactag ggatcggcgg | 840 | |
| atgtttcttc gatgactccg ccggcacctt atgagatatc aaagtttta gcttccgggg | 900 | |
| ggagtatggt cgcaaggctg aaacttaaag gaattgacgg aagggcacca ccaggcgtgg | 960 | |
| agcctgcggc ttaaggagac tcaacacggg aaaacttacg aggtccagac atagtgagga | 1020 | |
| ttgacagatt gagagctctt tcttgattct atgggtggtg gtgcatggcc gttcttagtt | 1080 | |
| ggtgggttgc cttgtcaggt tgattccggt aacgaacgag acctcagcct gctaaatagt | 1140 | |
| cacggttggt tcgccagccg gcggacttct tagagggaaa tgcctagtaa gcgc | 1194 | |

<210> SEQ ID NO 3
<211> LENGTH: 1327
<212> TYPE: DNA
<213> ORGANISM: Chlorella kessleri

<400> SEQUENCE: 3

| | | |
|---|---|---|
| cgtaaatccc gacttctgga agggacgtat ttattagatt taaggccgac ccggctctgc | 60 | |
| cggtctcgcg gtgaatcatg ataacttcac gaatcgcatg gccttgcgcc ggcgatgttt | 120 | |
| cattcttttt tctgccctat caactttcga tggtaggata gaggcctacc atggtggtaa | 180 | |
| cgggtgacgg aggattaggg ttcgattccg gagagggagc tgagaaacg gctaccacat | 240 | |

-continued

```
ccaaggaagc cagcaggcgc gcaaattacc caatcctgac acagggaggt agtgacaata    300
aatttcaata ccgggccttt tcaggtctgg taattggaat gagtacaatc taaacccctt    360
aacgaggatc aattggaggg caagtctggt gccagcagcc gcggtaattc cagctccaat    420
agcgtatatt taagttgctg cagttaaaaa gctcgtagtt ggatttcggg cggggcctgc    480
cggtccgccg tttgggtgtg cacaggcagg gcccgccttg ttgccgggga cgggctcctg    540
ggcttcactg tccgggactc ggagttggcg ctgttacttt gagtaaatta gagtgttcaa    600
agcaggccta cgctctgaat gcattagcat ggaataacac gataggactc tggcctatcc    660
tgttggtctg taggaccgga gtaatgatta agagggacag tcgggggcat tcgtatttcg    720
atgtcagagg tgaaattctt ggattttcga aagacgaact actgcgaaag catttgccaa    780
ggatgttttc attaatcaag aacgaaagat gggggctcga agacgattag ataccgtcct    840
agtctcaacc ataaacgatg ccgactagcg atcggcggat gtttcttcga tgactccgcc    900
ggcaccttat gagaaatcaa agtttttggg ttccgggggg agtatggtcg caaggctgaa    960
acttggggga attgacggaa gggcaccacc atgcgtggag cctgcggctt aatttgactc   1020
aacacgggaa aacttaccag gtccagacat agtgcggatt gacagattga gagctctttc   1080
ttgattctat gggtggtggt gcatggccgt tcttagttgg tgggttgcct tgtcaggttg   1140
attccggtaa cgaacgagac ctcagcctgc taaatcgtca cggcctcctc gggggccggc   1200
agacttctta gagggactat tggcgactag ccaatggaat catgaggcaa taacaggtct   1260
gtgatgccct tagatgccct gggccgcacg cgcgctactc tgatgcaatc aacgagccta   1320
gccttgg                                                             1327
```

```
<210> SEQ ID NO 4
<211> LENGTH: 1201
<212> TYPE: DNA
<213> ORGANISM: Botryococcus braunii

<400> SEQUENCE: 4
tatttattag ataaaaggct gaccgggctc gcccgactct tgctgactca tgataactcg     60
acggatcgca cgggcttgtc ccggcgacgt ttcattcgct tttctgccct atcaactgtc    120
gatggtacgg tagtggccta ccatggtgtt cacgggtgac ggagaattag ggttcgattc    180
cggagagggc gcctgagaga cggcgaccac atccaaggcc ggcagcaggc gcgcaaatta    240
cccaatcctg acacagggag gtagtgacaa taaataacaa tatcggggtt tccaaactct    300
gataattgga atgagtacaa tctaaaatcc ttaacgagga tcaattggag ggcaagtctg    360
gtgccagcag ccgcggtaat tccagctcca atagcgtata cccaagttgt tgcagttaag    420
ctgctcgtag tcggacttcg ggtgggggcc ggcggtccgc cgactggtgt gccatgccgg    480
gccccgcctt gctgccggag atgggatcct gggcttcgct gtccgggacc cggactcggc    540
gtggttactt tgagtaaatt agagtgttca aagcaggcct acgctctgaa tatgttagca    600
tggaataacg cgataggact ctggcctatc ttgttggtct gtgggaccgg agtaatgatt    660
aagagggaca gtcgggggca ttcgtatttc attgtcaggg gtgaaattct tggatttatg    720
aaagacggac tactgcgaaa gcatttgcca aggatgtttt cattgatcaa gaacgaaagt    780
tgggggctcg aagacgatta gataccgtcc tagtctcaac cataaacgat gccgactagg    840
gattggtggg tgttcttttg acgacccctc cagcacctta tgagaaatca aagtttttgg    900
gttccggggc gagtatggtc gtaaggctgg aacttaaagg aattgacgga agggcaccac    960
```

```
caggcgtgga gcctgcggct taatttgact caacacggga aaacttacca ggtccagaca    1020
tagtgaggat tgacagattg agagctcttc cttgattcta tgggtggtgg tgcatggccg    1080
ttcttagttg gtgggttggc ttgtcaggtt gattccggta acgaacgaga cctcagcctg    1140
ctaaatagtc cgaccaggtt cgcccaggcc gccgacttct tagagggact ctcggcgact    1200
a                                                                    1201

<210> SEQ ID NO 5
<211> LENGTH: 1200
<212> TYPE: DNA
<213> ORGANISM: Dunaliella salina

<400> SEQUENCE: 5
attagatggt acctttactc ggataaccgt agtaattcta gagctaatac gtgcgtaaat      60
cccgacttct ggaagggacg tatttattag ataaaaggcc agccgggctt gcccgactct     120
tggcgaatca tgataactta acgaatcgca cggctttatg ccggcgatgt ttcattcaaa     180
tttctgccct atcaactttc gatggtagga tagaggccta ccatggtggt aacgggtgac     240
ggaggattag ggttcgaccc cggagaggga gcctgagatt cggctaccaa atcccaggaa     300
ggcagcaggc gcgcaaatta cccaatccca acacggggat gtagtgacaa taataacaa      360 taccgggcat ttttgtctgg taattggaat gagtacaatc taaatccctt aacgagtatc     420
cattggaggg caagtctggt gaaagcagcc gcggtaattc cagctccaat agcgtatatg     480
taagttgttg cagttaaaaa gctcgtagtt ggatttcggg tgggttgtag cggtcagcct     540
ttggttagta ctgctacggc ctaccttcct gccgggacg agctcctggg cttaactgtc      600
cgggactcgg aatcggcgag gttactctga gtaaattaga gtgttcaaag caagcctacg     660
ctctgaatac attagcatgg aataacacga tcggactctg gcttatcttg ttggtctgta     720
agaccggagt aatgattaag agggacagtc ggggccattc gtatttcact gtcagaggtg     780
aaattcttgg atttttgaaag acgaacttcc tgcgaaagca tttgccaagg atgttttcat     840
taatccaaga acgaaagttg ggggctcgaa gacgattaga taccagtcgt agtctcaacc     900
ataaacgatg ccgacttagg gattggcagg tgtttcgttg atgaccctgc agcaccttt      960 atgagaaatc acagtttttt gggttccggg gggagtatgg tcgcaaggct gaaacttaaa    1020
ggaattgacg gaagggcacc accaggcgtg gagcatgcgg cttaattaga ctcaacacgg    1080
gaaaacttac caggtccaga cacggggagg attgacagat tgagagctct tcttgattc     1140 tgtgggtggt ggtgcatggc cgttcttagt tggtgggttg ccttgtcagg ttgattccgg    1200

<210> SEQ ID NO 6
<211> LENGTH: 1440
<212> TYPE: DNA
<213> ORGANISM: Nannochloropsis oculata

<400> SEQUENCE: 6
tataaactgc tttatactat gaaactgcga atggctcatt aaatcagtta tagtttattt      60
gatggtacct acttactcgg ataaccgtag taattctaga gctaatacgt gcgcacatcc     120
cgacttctgg aagggacgta tttattagat aaaaggccga ccggattttt ccgactcgcg    180
gtgactcatg ataacttcac gaatcgcatg gcctcgtgcc ggcgatgttt cattcaaatt     240
tctgccctat cggcttttga tggtaggata gaggcctacc atggtggtaa cgggtgacgg     300
agaattaggg ttcgattccg gagagggagc ctgagaaacg gctaccacat ccaaggaagg    360
cagcaggcgc gcaaattacc caatcctgac acagggaggt agtgacaata ataacaata     420
```

```
ccgggcettt ggtctggtaa ttggaatgag tacaacctaa acaccttaac gaggatcaat    480
tggagggcaa gtctggtgcc agcagccgcg gtaattccag ctccaatagc gtatatttaa    540
gttgctgcag ttaaaaagct cgtagttgga ttacgggtgg ggcctgccgg tccgccgttt    600
cggtgtgcac tggccgggcc caccttgttg ccggggacgg gctcctgggc ttcgctgtcc    660
gggacccgga gtcggcgagg ttactttgag taaaatagag tgttcaaagc aggcctacgc    720
tctgaataat tagcatggaa taacacgata ggactcaggc ctatcctgtt ggtctgtagg    780
accggagtaa tgattaagag ggacagtcgg gggcattcgt atttcattgt cagaggtgaa    840
attcttggat ttatgaaaga cgaactactg cgaaagcatt tgccaaggat gttttcatta    900
atcaagaacg aaagttgggg gctcgaagac gattagatac cgtcctagtc tcaaccataa    960
acgatgccga ctagggatcg gcgggtgttt ttttgatgac cccgccccca ccttatgaga   1020
aatcaaagtt tttgggttcc gggggagta tggtcgcaag gctgaaactt aaaggaattg   1080
acggaagggc accaccaggc gtggagcctg cggcttaatt tgactcaaca cgggaaaact   1140
taccaggtcc agacatagtg aggattgaca gattgagagc tctttcttga ttctatgggt   1200
ggtggtgcat ggccgttctt agttggtggg ttgccttgtc aggttgattc cggtgacgaa   1260
cgagacctca gcctgctaac tagtcacgcg tgctccggca cgcggcggac ttcttagagg   1320
gactattggc gactagccaa tggatgcatg aggcaataac aggtctgtga tgcccttaga   1380
tgttctgggc cgcacgcgcg ctacactgat gcattcaacg agcctatcct tggccgagag   1440
```